United States Patent [19]

Durette

[11] Patent Number: 4,868,157

[45] Date of Patent: Sep. 19, 1989

[54] DIPEPTIDYL 2-AMINO-1,2-DIDEOXY-D-GLUCOSE DERIVATIVES AS HOST RESISTANCE ENHANCERS IN AIDS-IMMUNOCOMPROMISED HOSTS AND METHODS OF USE

[75] Inventor: Philippe L. Durette, New Providence, N.J.

[73] Assignee: Merck & Co., Inc., Rahway, N.J.

[21] Appl. No.: 105,051

[22] Filed: Oct. 5, 1987

[51] Int. Cl.$^4$ .................... A61K 37/02; A61K 39/00; C07C 103/52
[52] U.S. Cl. ......................................... 514/19; 514/9; 514/21; 514/42; 514/44; 514/46; 514/50; 514/75; 514/78; 514/357; 260/396 R
[58] Field of Search ................. 514/19, 9, 2, 21, 42, 514/44, 46, 50, 75, 78, 357; 424/88, 89, 92; 530/322; 548/535; 260/396 R

[56] References Cited

U.S. PATENT DOCUMENTS 4,315,913 2/1982 Durette ............................... 424/88

OTHER PUBLICATIONS

Dagani, "Efforts Intensify to Develop Drugs, Vaccines that Combat AIDS", C&E News, Dec. 8, 1986, pp. 7–14.

Primary Examiner—John Kight
Assistant Examiner—Nathan M. Nutter
Attorney, Agent, or Firm—Robert J. North; John W. Harbour

[57] ABSTRACT

Disclosed are specific dipeptidyl 2-amino-1,2-dideoxy-D-glucoses which, either alone, or in combintion with an anti-AIDS drug, e.g. azidothymidine, protect an immunocompromised human host, resulting from an AIDS-related virus, against opportunistic, bacterial, fungal and viral infections, as well as help to suppress the AIDS-related virus itself.

4 Claims, No Drawings

DIPEPTIDYL 2-AMINO-1,2-DIDEOXY-D-GLUCOSE DERIVATIVES AS HOST RESISTANCE ENHANCERS IN AIDS-IMMUNOCOMPROMISED HOSTS AND METHODS OF USE

BACKGROUND OF THE INVENTION

1. Field of the Invention

Disclosed are specific dipeptidyl 2-amino-1,2-dideoxy-D-glucoses which, either alone, or in combination with an anti-AIDS drug, e.g. azidothymidine, protect an immunocompromised human host, resulting from an AIDS-related virus, against opportunistic bacterial, fungal and viral infections.

2. Brief Description of Disclosures in the Art

The search for new immunostimulants capable of augmenting host defenses to combat infection, cancer and congenital immunodeficiency disorders is an increasingly important area of pharmaceutical endeavor particularly as it relates to AIDS related viruses.

Seven years ago few had ever heard of acquired immune deficiency syndrome, or AIDS. This puzzling affliction, then seen in only a small number of young, homosexual men, was something new and unnamed. Today, it's hard to find anyone in the U.S. who hasn't heard of AIDS, the disease that can debilitate and then kill its victim with horrific swiftness.

AIDS has come to be recognized as a public health emergency. More than 27,700 American men, women, and children have been stricken by it; the death toll is 16,000 and rising. The U.S. Public Health Service predicts that by the end of 1991 more than 179,000 persons will have succumbed to the disease.

Thus far, there is no cure for AIDS.

Technically, acquired immune deficiency syndrome (AIDS) is a transmissible deficiency of cellular immunity characterized by opportunistic infections and certain rare malignancies. The dominant risk groups for AIDS include homosexually active males, intravenous drug abusers, recipients of transfusions and blood products, and the heterosexual partners and children of high risk individuals, suggesting the involvement of an infectious agent transmitted through intimate contact or blood products.

Recent evidence indicates that the infectious agent responsible for disease transmission is a novel lymphotropic retrovirus, currently designated HIV-I (human immunodeficiency virus) and also known as lymphadenopathy -associated virus (LAV) (Barré-Sinoussi et al., Science 220: 868 (1983)). Similar viruses have been reported by other scientific groups (Popovic et al., Science 224: 497 (1984); Levy et al. Science 25: 840 (1984)) and designated human T cell lymphotropic virus type III (HTLV III), AIDS-associated retrovirus (ARV), or immune deficiency-associated virus (IDAV). Still more recent data indicates that LAV, HTLV III, ARV and IDAV share several important characteristics, including substantial nucleotide homology (Wain-Hobson et al., Cell 40: 9 (1985); Muesing et al., Nature 313: 450 (1985); Sanchez-Pescador et al., Science 227: 484 (1985)), and should be considered isolates of the same virus, although there is a likelihood that strain-to strain variations among the viral isolates will exist. In addition to exhibiting substantial nucleotide homology, the isolates are similar with respect to morphology, cytopathology, requirements for optimum reverse transcriptase activity, and at least some antigenic properties (Levy, supra: Schupbach et al., Science 224: 503 (1984)). The above materials are hereby incorporated by reference to characterize the phrase "AIDS related virus".

U.S. Pat. No. 4,315,913 to Durette (assigned to Merck & Co., Inc.) describes immunologically active, dipeptidyl 2 amino-1,2-dideoxy-D-glucose derivatives, and methods of preparation, described herein, which reference is incorporated herein by reference for this particular purpose.

However, the above disclosure does not specifically describe use of the compounds alone, or in combination with an anti-AIDS drug, e.g. azidothymidine, for use as host resistance enhancing agents, i.e., immunostimulators specifically to combat viral, fungal and bacterial infections in AIDS-immunocompromised hosts.

SUMMARY OF THE INVENTION

In accordance with the present invention, there is provided a method of enhancing the host resistance to opportunistic infection in an AIDS-immunocompromised human host comprising the step of administering to said host a composition containing a compound of the formula (I):

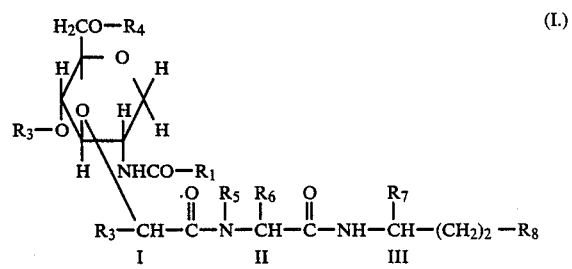

wherein:

$R_1$ is $C_{1-7}$ alkyl, substituted $C_{1-7}$ alkyl; phenyl; or substituted phenyl;

$R_2$ is hydrogen; or $C_{1-10}$ alkyl;

$R_3$ and $R_4$ may be the same or different and are each independently hydrogen or acyl of the formula:

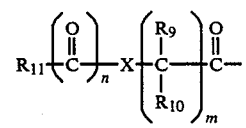

where X is —O—, —S—, —CH$_2$—,

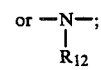

$R_9$, $R_{10}$, and may be the same or different and are each independently hydrogen; $C_{1-20}$ alkyl; $C_{2-20}$ alkenyl; $C_{1-20}$ alkyl-carbonyloxy; amino; phenyl; benzyl; $C_{1-20}$ alkoxymethyl; or $C_{1-20}$ alkylamido;

$R_{11}$ is hydrogen; $C_{1-30}$ alkyl; $C_{2-30}$ alkenyl; $C_{1-30}$ alkoxy; phenyl; $C_{1-20}$ alkylsulfonyl; or cholesteryl;

and m is 0–90; and n is 0 or 1, provided that when n is 0, $R_{11}$ may additionally be phenyl, substituted phenyl, 1-adamantyl, or heterocycle selected from the group consisting of 2- or 3-furyl, 2- or 3-thienyl, 2- or 3-pyrrolidinyl, 2-, 3-, or 4-pyridyl, and 1-tetrazolyl, said heterocycle optionally substituted with $C_{1-20}$ alkylcarbonyl;

$R_5$ is hydrogen; or $R_5$—$R_6$ together is —$CH_2$—$CH_2$—$CH_2$;

$R_6$ is hydrogen; $C_{1-7}$ alkyl; hydroxymethyl; mercaptomethyl; benzyl; or substituted benzyl;

$R_7$ and $R_8$ may be the same or different and are each independently COOR or CONR'R'', where R is hydrogen or $C_{1-7}$ alkyl, and R' and R'' are each independently hydrogen or $C_{1-3}$ alkyl;

when $R_2$ is $C_{1-10}$ alkyl, the stereochemistry at asymmetric center I can be either D or L;

when $R_6$ is not hydrogen, the stereochemistry at asymmetric center II is L; the stereochemistry at asymmetric center III is D; and pharmaceutically acceptable salts thereof, in a physiologically acceptable medium in an amount effective to impart resistance to viral, bacterial, fungal infection in an AIDS-immunocompromised host.

Also provided is a pharmaceutical composition containing the above-described compounds in combination with an anti-AIDS drug for treating a human in an AIDS-immunocompromised human host.

Also provided is a method for enhancing resistance in a human host immunocompromised by an AIDS-related virus comprising administering to said host a pharmaceutical composition, as described above, in which method, the anti-AIDS drug can be administered in combination, concurrently or separately, with the indicated compound.

Specifically provided is where the composition contains an anti-AIDS drug selected from one or more of the following: azidothmidine, AL 721, ampligen, ansamycin, azimexon, cyclosporine, foscarnet, HPA-23, imreg-1, inosine pranobex, alpha-interferon, interleukin-2, D-penicillamine, ribavirin, suramin, CS-85, 2',3'-dideoxycytidine, 2',3'-dideoxyadenosine, gamma interferon, RNA deriv, Immune globulin IG-IV, thymopentin, thymostimulin, methionine-enkephalin or equivalents thereof.

DETAILED DESCRIPTION OF THE INVENTION AND PREFERRED EMBODIMENTS

The glycopeptide compositions described herein provide very high levels of protection against opportunistic infections in immunocompromised animals and humans.

By the term "AIDS-related virus" is meant the commonly designated HIV series (human immunodeficiency virus) formerly called HTLV and LAV, and species thereof, as described above in the indicated incorporated references.

These compositions may be used prophylactically to protect immunosuppressed animals or patients against infection by opportunistic organisms. In human medicine, the market includes surgery patients, burn victims, cancer patients receiving chemotherapy, aplastic anemics, diabetics, and military recruits. In animal health, the primary potential use markets include major segments of the worldwide economic animal populations during stressful shipping, mixing, and early life adaptation periods.

By the term "immunostimulant", as used herein, is meant a material which can be employed to potentiate a non-specific immune response on the part of the host.

The composition of the present invention does not contain specific antigens per se. Rather, the composition contains only immunostimulants for producing a generalized and nonspecific immunological response on the part of the host, and further includes acceptable salts, carriers, diluents, vehicles and the like for intravenous, subcutaneous or intraperitoneal administration.

In the description for formula I, the term "substituted $C_{1-7}$alkyl" for $R_1$ refers to an alkyl group of from 1 to 7 carbon atoms substituted by hydroxy, mercapto, alkoxy of 13 carbons, alkylmercapto of 13 carbons, hydroxy or mercapto esterified by an acid of 1–4 carbon atoms, halogen (F, Cl or Br), carboxyl, or carboxyl functionally modified by esterification with a lower alcohol of 1–3 carbons or by amidation. Preferably, the alkyl substituents are hydroxy or mercapto, either free or substituted by an alkyl group of 1–3 carbons.

The substituents in the term "substituted phenyl" and "substituted benzyl" for $R_1$ and $R_6$, refer to the phenyl or benzyl group substituted by one or more alkyl groups of 1–3 carbon atoms or hydroxy or mercapto groups either free, or etherified by an alkyl group of 1–3 carbons or esterified by an acid of 1–4 carbons, lower (1–4C) alkyldioxy, cycloalkyldioxy of 5–7 carbon atoms, amino, trifluoromethyl, halo, or phenyl.

The substituents in the term "substituted phenyl" for $R_{11}$ are halo or phenyl.

For $R_7$ and $R_8$, among the optionally esterified carboxyl groups can be mentioned the carboxyl group esterified by a lower alcohol of 1–3 carbons, like methanol or ethanol. The carboxyl group can also be amidated, unsubstituted at the nitrogen atom or mono or di-substituted with an alkyl, in particular, a lower alkyl, an aryl, particularly phenyl, or an aralkyl, particularly benzyl.

Most preferably, $R_1$ is alkyl of 1–3 carbons, phenyl or phenyl p substituted by alkyl (1–3C), amino, halogen, hydroxy or trifluoromethyl; $R_6$ is preferably hydrogen, alkyl of 1–4 carbons, hydroxymethyl, mercapto-methyl, benzyl or p-hydroxy benzyl; and preferably $R_5$ and $R_6$ together are —$CH_2CH_2CH_2$—.

The obtained compounds can be transformed to their salts in a classical fashion, for example, by reacting the acidic compounds obtained with alkaline or alkaline earth hydroxides, or the basic compounds with acids.

The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2 naphthalenesulfonate, nicotinate, oxalate, pamoate, pectinate, persulfate, succinate, tartrate, thiocyanate, tosylate, and undecanoate. Also, the basic nitrogen-containing groups can be guaternized with such agents as lower alkyl halides, such as methyl, ethyl, propyl, and butyl chlorides, bromides and iodides; dialkyl sulfates like dimethyl, diethyl-, dibutyl, and diamyl sulfates; long chain halides such as decyl, lauryl, myristyl and stearyl chlorides, bromides and iodides; aralkyl halides like benzyl and phenethyl bromides and others. Water or oil soluble or dispersible products are thereby obtained.

The compounds in the present invention possess immunostimulatory properties and may be used as immunomodulating agents, i.e. to stimulate the host immune response. They are especially useful for increasing the host response against viral infections.

The pharmaceutically acceptable compounds of the present invention can be used, for example, for the manufacture of pharmaceutical preparations that contain a pharmaceutically effective amount, for example an amount sufficient for immunostimulation, of the active ingredient together or in admixture with a significant amount of inorganic or organic, solid or liquid pharmaceutically acceptable carriers.

The pharmaceutical preparations according to the invention are for enteral, such as oral or rectal, and parenteral, such as intraperitoneal, intramuscular or intravenous, administration to warm-blooded animals and contain the pharmacological active ingredient alone or together with a pharmaceutically acceptable carrier.

The carriers may be inorganic or organic and solid or liquid. For example, there are used tablets or gelatine capsules that contain the active ingredient together with diluents, for example F2: lactose, dextrose, sucrose, mannitol, sorbitol, cellulose and/or glycerine, and/or lubricants, for example silica, talc, stearic acid or salts thereof, such as magnesium or calcium stearate, and/or polyethylene glycol. Tablets may also contain binders, for example magnesium aluminium silicate, starches, such as corn, wheat or rice starch, gelatine, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, colorings, flavorings and sweeteners. The pharmacologically active compounds of the present invention can also be used in the form of parenterally administrable preparations or in the form of infusion solutions. Such solutions are preferably isotonic aqueous solutions or suspensions, it being possible, for example in the case of lyophilized preparations that contain the active ingredient alone or together with a carrier, for example mannitol, for these to be manufactured before use. The mentioned solutions or suspensions may contain viscosity-increasing substances, such as sodium carboxymethylcellulose, carboxymethylcellulose, dextran, polyvinylpyrrolidone or gelatine. The pharmaceutical preparations may be sterilized and/or contain adjuncts, for example preservatives, stabilizers, wetting agents and/or emulsifiers, solubilizers, salts for regulating the osmotic pressure and/or buffers. The present pharmaceutical preparations which, if desired, may contain other pharmacologically active ingredients, such as antibiotics, are manufactured in a manner known per se, for example by means of conventional mixing, granulating, confectioning, dissolving or lyophilizing processes, and contain approximately from 0.001% to 99%, especially from approximately 0.01% to approximately 10%, more especially from 0.1% to 5%, of the active ingredient(s), an active ingredient concentration of less than 1% being especially suitable for preparations that are to be applied topically.

Pharmaceutical preparations according to the invention may be, for example, in dosage unit form, such as dragees, tablets, capsules, suppositories or ampoules.

Pharmaceutical preparations for oral administration can be obtained by combining the active ingredient with solid carriers, optionally granulating a resulting mixture and processing the mixture or granulate, if desired or necessary after the addition of suitable adjuncts, to form tablets or dragee cores. It is also possible to incorporate them into synthetic carriers that release the active ingredients, or allow them to diffuse, in a controlled manner.

The manufacture of injection preparations is carried out in customary manner under antimicrobial conditions, as is the filling into ampoules or phials and the sealing of the containers.

Furthermore, the compounds of the present invention provide, alone, or in combination with "anti-AIDS drugs", human host protection against opportunistic infections in individuals immunocompromised by an AIDS-related infectious organisms in addition to their direct therapeutic effect against the AIDS-related virus. These include fungal, viral and bacterial, including the specific conditions of Kaposi's sarcoma and pneumocystis pneumonia. They are also capable of potentiating antibiotic activity. By the term "anti-AIDS drugs" is meant therapeutic drugs which are thought to act directly or indirectly against the AIDS-related virus by a variety of known or unknown mechanisms.

The following anti-AIDS drugs are currently being investigated and are known to exhibit either some antiviral or immunomodulatory effect in a human host against the AIDS-related virus (from *Chemical & Engineering News*, Dec. 8, 1986, pp 7-14, hereby incorporated by reference for this purpose):

AL 721: Lipid mixture composed of neutral glycerides, phosphatidylcholine, and phosphatidylethanolamine in 7:2:1 ratio. Interferes with HIV infectivity but not by inhibiting reverse transcriptase; possibly it disrupts the virus's membrane. No adverse effects observed during a six-week clinical trial.

Ampligen: Mismatched double-stranded RNA polynucleotide that induces the body to release interferon, thus stimulating antiviral activity. Reportedly does not have side effects of interferon injections. Currently undergoing preliminary clinical trials in AIDS patients.

Ansamycin (rifabutin, $C_{45}H_{29}N_4O_{11}$): Italian antibacterial drug, a member of the rifamycin group of antibiotics, which are characterized by a natural ansa structure (chromophoric naphthohydro quinone group spanned by a long aliphatic bridge). Drug has shown some efficacy in treating AIDS patients with an opportunistic infection caused by the bacterium *Mycobacterium aviumintracellulare*.

Azidothymidine: (AZT, 3'azido-3'-deoxythymidine, zidovudine). First drug to show promise in prolonging lives of patients with AIDS or AIDS-related complex (ARC). Well absorbed orally and effectively penetrates central nervous system, but has relatively short half-life in the body and some toxicity, with anemia and headaches. ARC patients treated with AZT showed virtually no toxic effects.

Azimexon: Cyanaziridinyl immunemodulator. Early trial showed improvements in symptoms and immune function in patients with ARC but not AIDS; only toxic effect was mild hemolysis (disintegration of red blood cells with release of hemoglobin), which disappeared when treatment ceased.

Cyclosporine (cyclosporin A): Cyclic undecapeptide with potent immunosuppressive effects, used in cancer therapy. Inhibits T4 lymphocyte-dependent immune responses. Basis of controversial AIDS therapy in France; rationale is that HIV infects "activated" T4 cells, which are primed to defend the body, so drug that prevents activation of T4 cells may limit progression of disease. The French claim encouraging results with it.

Foscarnet (trisodium phosphonoformate): Swedish drug that has been used to treat CMV infection in immunocompromised patients, also to treat herpes. Inhibits HIV reverse transcriptase activity in vitro at levels pharmacologically acceptable in vivo. Formulation problems and serious side effects have been encountered. No results yet reported in HIV-infected patients.

HPA-23 (ammonium 21-tungsto-9-antimoniate), $[(NH_4)_{18}(NaW_{21}Sb_9O_{86})_{17}]$: Inhibits reverse transcriptase in several retroviruses in vitro, but mechanism of antiviral action against HIV is unknown. Drug has shown some tendency to check the growth of HIV, but no therapeutic benefit has been documented in AIDS patients.

Imreg-1: Proprietary immunemodulator derived from white blood cells. Reportedly can enhance production of other biological response modifiers such as interleukin-2 and $\gamma$-interferon, which are critical to normal functioning of immune system.

Inosine pranobex (isoprinosine, inosiplex): p-Acetamidobenzoic acid salt of (1-dimethylamino-2-propanol:inosinate complex 3:3:1 molar ratio). Chemically synthesized antiviral and immunemodulator originally developed to enhance memory in elderly. In one study, found to improve immune function in ARC patients.

$\alpha$-Interferon: Glycoprotein produced by cells in response to virus infection; helps amplify or regulate immune responses. Checks the growth of HIV in vitro. Has induced tumor regression in some AIDS-related Kaposi's sarcoma cases. Not known whether $\alpha$-interferon has anti-HIV activity in vivo.

Interleukin-2 (IL-2): Protein made by white blood cells that mediates production of interferon. Inability to produce IL-2 may predispose AIDS patients to opportunistic infections. Preliminary results of therapy with recombinant IL-2 not encouraging, but trials continue.

D-Penicillamine (3-mercapto-D-valine): Used to treat rheumatoid arthritis and Wilson's disease, a rare copper storage disease. Inhibits HIV reproduction in humans. In trials at George Washington University Medical Center, it suppressed the virus but also temporarily depressed T cell levels in 13 AIDS patients with perpetually swollen glands.

Ribavirin (1-$\beta$-D-ribofuranosyl-1,2,4-triazole-3-carboxamide): Synthetic nucleoside used to treat a viral respiratory infection in children. In early clinical trials, it inhibited viral replication and improved immune function in AIDS patients. Longer (24-week) trial in 373 ARC patients has been completed; at 12 weeks, ribavirin's safety profile was judged to be acceptable, and the drug was found to be well tolerated.

Suramin ($C_{51}H_{34}Na_6O_{23}S_6$): Antiparasitic agent. Potent inhibitor of HIV reverse transcriptase, but also significantly inhibits desirable biological functions. In AIDS patients, it has produced little or no evidence of clinical improvement or immunologic recovery. Has serious side effects, inability to penetrate central nervous system. Not considered appropriate for single-agent use in AIDS. No longer being actively pursued.

Furthermore, the U.S. Food and Drug Administration has released a list of 16 proposed AIDS treatments which have received IND status. The list contains only treatments which "have been publicly acknowledged by their sponsors", and therefore some experimental treatments may have been omitted.

| Experimental treatment | Sponsor |
| --- | --- |
| Immunomodulators | |
| Thymopentin | Ortho Pharmaceuticals |
| Thymostimulin | Serono Laboratories |
| Methionine-enkephalin | National Jewish Hospital |
| Isoprinosine | Newport Pharmaceuticals |
| Antivirals | |
| Ansamycin | Adria Laboratories |
| Ribavirin | Viratek/ICN Pharmaceuticals |
| Dideoxycytidine (DDC) | National Cancer Institute |
| HPA-23 | Rhone-Poulenc |
| AL-721 | Matrix Laboratories[1] |
| Foscarnet | National Institute of Allergy and Infectious Diseases |
| Biologicals | |
| Alpha-interferon | Hoffmann-La Roche |
| Gamma-interferon | Genentech |
| Imreg-1 | Imreg Inc |
| Interleukin-2 | Hoffmann-La Roche |
| RNA deriv | HEM Research |
| Immune globulin IG-IV | Sandoz Pharmaceuticals and Alpha Therapeutics |

[1] a subsidiary of Praxis Pharmaceutical;

Further, Yakult's immunostimulant, LC-9018, and two herbal products, shosaikoto and ginseng, being studied by Tsumura Juntendo, may be of benefit in patients with AIDS.

LC-9018 has been found to be about 20 times more potent than Ajinomoto's lentinan in inducing macrophage activation, and it is undergoing clinical trials in AIDS patients in the U.S., note the analysts. Phase III trials with LC-9018 in patients with cancer are currently underway in Japan. Shosaikoto and ginseng have been found to increase depleted helper T-cell counts in seven of nine AIDS-carriers studied by researchers at Tsumura Juntendo and Tokyo Medical University.

Furthermore, HEM Research's potential anticancer agent, ampligen (a mismatched double-stranded RNA), reduces at least five-fold the concentration of Wellcome's azidothymidine (Retrovir) required for inhibitory activity against human immunodeficiency virus (HIV) in vitro, (*The Lancet* April 18th, p. 890). Ampligen is currently in Phase II clinical trials as an anticancer agent and HEM is seeking partners to fund a clinical trial in AIDS.

At higher concentrations of azidothymidine, there seemed to be a synergistic relation between the two compounds, since complete protection was provided by combined suboptimal doses of each drug. Ampligen could reduce the dose of azidothymidine required for a therapeutic effect in vivo, so reducing its toxicity.

Since the two drugs have entirely different modes of action, it is unlikely that they will exert toxicities other than those associated with each drug alone. In recent clinical studies, "virtually no toxicity" was associated with intravenous ampligen. Moreover, since ampligen has clinically demonstrated immunological as well as antiviral activity, its use together with azidothymidine may have pronounced and long-term beneficial effects on the course of AIDS beyond that which can be estimated in vitro.

In addition, CS-85, or 3'-azido-2',3'-dideoxy-5-ethyl-(uridine), developed by Raymond F. Schinozi at the Veterans Administration Medical Center and Emory University, both in Atlanta, Ga., shows promise.

All of the above-described compounds are deemed to be included within the scope of the term "anti-AIDS drug" as used herein. Use of more than one of these compounds, in addition to the glycopeptide of structure I, in the combination composition is contemplated.

The composition containing the glycopeptide compounds and an above described anti-AIDS drug will contain the glycopeptide in an amount as described above and the anti-AIDS drug in an amount, based on the glycopeptide, in a weight ratio of 1:3 to 3:1 and preferably 1:1 based on the weight of glycopeptide.

The dosage form of the combination drug will be 1 to 50 mg/kg of human body weight per day and preferably 2.5 to 40 mg/kg.

The method of co-administering the two ingredients, if not using the combination composition, can be separately, concurrently or simultaneously.

The obtained compounds can be transformed to their salts in a classical fashion, for example, by reacting the acidic compounds obtained with alkaline or alkaline earth hydroxides, or the basic compounds with acids.

The present invention is also directed to pharmaceutical preparations that contain a compound of Formula II. Among the pharmaceutical preparations relevant to this invention are salts that are administered by external route, for example, orally, rectally or parenterally to human species. Preparations may be administered that contain the pharmacologically active compound by itself or mixed with a pharmacologically acceptable carrier. The dose of the pharmacologically active compound depends on the sex, the age, and the state of the human individual and the mode of application.

The new pharmaceutical preparations contain from about 10% to about 95% and, preferably from about 20% to about 90% of a compound of the present invention. The pharmaceutical preparation relevant to this invention can be presented, for example, in the form of unit doses like tablets, capsules, suppositories, and ampoules.

Also a subject of the invention is a method for administering to an immunocompromised host a composition as described herein, containing a compound of the formula (I), as described, contained in a suitable carrier which may or may not have additional material such as diluents and other materials which may be deemed necessary under the circumstances. However, it is understood that the immunostimulatory preparation does not in fact include a specific antigen as a composition component.

The following examples exhibit the subject invention as contemplated by us and should not be construed as being limiting with respect to the scope and nature of the instant invention.

The immunostimulatory properties of the compounds in the present invention can be demonstrated with the following protocols:

1. In vivo Stimulation of Humoral Response: Increase in the Production of Antibodies Against Bovine Serum Albumin (BSA) in the Mouse Mice (NMRI) are immunized by i.p. injections of 10 mg of BSA without precipitate. At 0, 9, 15 and 29 days later blood samples are taken and analyzed for anti-BSA-antibody titers by the passive hemagglutination technique. At the dose utilized, soluble BSA is subimmunogenic for the receiving animals, that is, it does not cause any antibody production, or at most a completely insignificant production. Additional treatment of the mice with certain immunostimulants before or after administration of antigen leads to an increase in antibody titer in the serum. The effect of the treatment is expressed by the obtained score, that is, the sum of the logs to the base 2 of the differences of the titer at 3 days of bleeding.

The compounds of the present invention are capable of augmenting in a significant manner the production of anti-BSA antibodies by i.p. or subcutaneous application (s.c.) of 100–300 mg/kg/animal during 5 consecutive days (day 0 to day 4) after immunization with BSA.

The immunostimulatory effect of the compounds mentioned herein depend on the antigen, contrary to other bacterial immunostimulants (like LPS of $E.\ coli$). The injection of the compounds of the present invention results in augmentation of anti BSA antibody titer only in mice immunized with BSA, and not with non-immunized mice. Subcutaneous administration is as efficacious as i.p., that is, the immunostimulatory effect observed is systemic and does not depend on the fact that the stimulant was administered by the same route as the antigen or mixed with it, as is the case with classical adjuvants.

The compounds of the present invention permit specific augmentation of humoral immunity, improve immune response, and provide long lasting immunostimulatory effects on systemic activation of immune apparatus.

2. Stimulation of Mitotic Responses of Lymphocyte Cultures

Mouse lymphoid cells are cultured in microtiter plates, in RPMI-1640 medium with 2% fetal calf serum. Cultures are set in triplictes and consist of $3–5 \times 10^5$ spleen or $1.5 \times 10^6$ thymus cells per well in a final volume of 0.2 ml. Class specific mitogens are added at optimal or suboptimal concentrations, while control cultures are incubated without mitogen. The tested compounds are added shortly after the mitogens and the cultures are incubated for 48 hours at 37° with 5% $CO_2$. Incorporation of tritiated thymidine is determined after a pulse (1.0 $\mu$Ci/well) during the last 6 hours in culture. The data are recorded as mean cpm and the effects of the compounds are presented as stimulation index (mean cpm in cultures with the compound/mean cpm in control).

The compounds of the present invention enhance the levels of thymidine incorporation in lymphocyte cultures, with or without mitogens. The stimulation indices are maximal in control cultures or in those with suboptimal doses of mitogens. Similar effects of the compound are provoked in cultures of different lymphocyte populations, namely, B cells (nude spleen), T cells (thymus) or their mixtures (normal spleen). The effects of the compounds are dose dependent. These compounds, therefore, are capable of stimulating proliferation of lymphocytes that participate in the humoral response (B cells) as well as in cellular immunity (T cells).

3. Compatibility

Although the compounds of the present invention produce their stimulatory effect with guinea pigs, for example, beginning with a single dose of 0.05 mg/kg s.c., and with mice after 5 applications of 10 mg/kg s.c., no toxic effect is observed after 5 applications of 300 mg/kg i.p., with the mouse. These compounds possess, therefore, a remarkable therapeutic index.

The compounds of the present invention thus have the capacity, by systemic application, of increasing the immunological reactivity of the treated organism. Moreover, these compounds can enhance cellular as well as humoral immunity and activate lymphocytes responsible for the formation of antibodies.

The compounds of the present invention can consequently be employed as protective agents against infections caused by bacteria, viruses or pathogenic parasites, owing to immnunity by humoral antibodies and/or to cellular mediation.

These compounds are therefore especially indicated for stimulation of individual immune defense, e.g., at the time of chronic or acute infections or in cases of selective (antigen-specific) immunological deficiencies as well as in situations of immune deficiency, but also acquired general deficiency (i.e., not antigen-specific) as appears with age, during initial shock from a grave illness, and before and soon after radiation therapy or immunosuppressive hormones. The said compounds can subsequently be administered in combination with anti-infectious antibiotics, chemical therapeutics or other methods of treatment, to combat immunological deficiencies. The described compounds are thus indicated equally for general prophylaxis of infectious disease in man and animal.

Intermediates for the compounds of Formula I may be prepared by condensing, using conventional procedures, a protected compound of Formula II with a protected compound of Formula III:

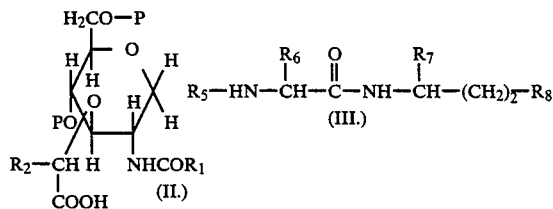

In the foregoing formulas, $R_1$, $R_2$, $R_5$, $R_6$, $R_7$, and $R_8$ represent the groups mentioned previously while P is a protecting group. The protecting group may be any suitable to protect the group to which it is attached during the condensation reaction and which may be readily removed thereafter. As protecting groups for the carboxyl group in the dipeptide of Formula III, there may be mentioned tertiary-butyl, benzyl or benzhydryl. For the hydroxyl groups in Formula II intermediates, there may be mentioned alkyl radicals, such as tertiary-butyl, benzyl, nitrobenzyl, lower alkoxy radical, or the tetrahydropyranyl radical. In addition, there may be mentioned the optionally substituted alkylidene radicals that block the oxygen atoms at the C-4 and C-6 positions. Among the alkylidene radicals, one finds, in particular, the lower alkylidene radicals, especially ethylidene, isopropylidene, or propylidene, and also, the optionally substituted benzylidene radical, preferentially substituted at the para position. For a more complete listing of protecting groups, reference may be had to standard works on peptide chemistry, e.g., Bodanszky et al., "Peptide Synthesis", chapter 4, Interscience Publishers (1966), or Schroeder et al., "The Peptides", Vol I, pp. xxiii–xxix, Academic Press (1965), and to the text "Protective Groups in Organic Chemistry", Plenum Press (1973), J. F. W. McOmie (ed.).

The condensation is effected by reacting the compound II in the form where the carboxylic acid is activated with the amino compound III. The activated carboxyl group may be, for example, an acid anhydride, preferably, a mixed acid anhydride like an acetate of the acid, an amide of the acid like an imidazolid, an isozazolid, or an activated ester. The activated esters, include the cyanomethyl ester, the carboxymethyl ester, the p-nitrophenyl thioester, the p-nitrophenyl ester, the 2,4,5-trichlorophenyl ester, the pentachlorophenyl ester, the N-hydroxy succinimide ester, the N-hydroxyphthalimide ester, the 8-hydroxyquinoline ester, the 2-hydroxy-1,2dihydro-1-carboethoxyquinoline esters, the N hydroxypiperidine ester or enol ester derived from N-ethyl-5-phenyl-isoxazolium-3'-sulfonate. The activated esters may equally be obtained from a carbodiimide by addition of N-hydroxysuccinimide or from a substituted 1-hydroxybenzotriazole for example, a halogen, methyl, or methoxy substituted 3-hydroxy-4-oxo-3,4-dihydrobenzo[d]1,2,3-triazine.

The amino group may be activated, for example, by reaction with a phosphitamide.

Among the methods of reaction with the activated esters, one must mention in particular those that involve N-ethyl-5-phenyl-isoxazolium-3'-sulfonate (Woodward's Reagent K), N-ethoxycarbonyl-2-ethoxy-1,2-dihydroquinoline, or carbodiimide.

The starting materials utilized are known or can be made in a known fashion. Thus, one can obtain compounds of Formula II, for example, by reacting the corresponding sugar unsubstituted at position-3 with a halogen-$R_2$-acetic acid where $R_2$ has the meaning mentioned above. The ether is obtained in the presence of a strong base. The halogen is preferentially bromo or chloro.

Another process of synthesizing intermediates for the compounds of Formula I consists of condensation, and eventual removal in conventional manner of the protecting groups, a compound of Formula IV,

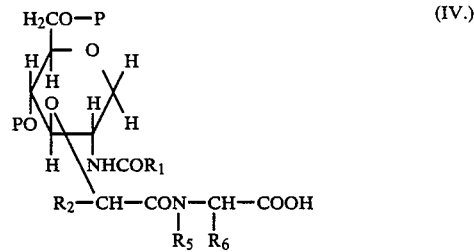

wherein $R_1$, $R_2$, $R_5$, and $R_6$, and P have the meaning mentioned above, with a compound of Formula V:

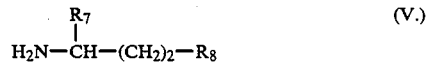

wherein $R_7$ and $R_8$ have the meaning mentioned above.

The condensation may be effected by reacting compound IV in the form of an activated carboxylic acid with the amino compound of Formula V, or by reacting the Formula IV compound in the form of the free C-terminal carboxyl group with the Formula V compound where the amino group is present in activated form. The activated carboxyl group can be, for example, an acid anhydride and preferably a mixed acid anhydride, an acid amide or an activated ester. Among these, one finds in particular the acid anhydrides, the amides, or the esters mentioned above. The amino group may be activated, for example, by reaction with a phosphitamide. The readily removable protecting groups correspond to those mentioned above.

The starting materials are obtained in classical fashion. One can, therefore, react the corresponding sugar unsubstituted at position-3 with halogen-$R_2$-acetamido-$R_6$-acetic acid or a compound of Formula II with an amino-$R_6$-acetic acid where the carboxyl group is blocked as mentioned above.

Another process for inserting the side chain at position-3 of the sugar radical consists in reacting a compound having the following structure:

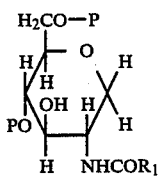
(VI.)

where $R_1$ and P have the signification mentioned above, with a compound of Formula VII:

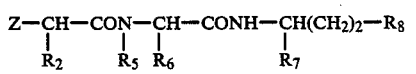
(VII.)

where Z represents an esterified hydroxy group capable of reacting and wherein $R_2$, $R_5$, $R_6$, $R_7$ and $R_8$ have the meaning given above. An esterified hydroxy group capable of reacting is, first of all, a hydroxy group esterified with a strong inorganic or organic acid and especially a group esterified by the hydrohalic acids, like hydrochloric acid, hydrobromic acid, or hydroiodic acid. The protecting groups correspond to those already mentioned above. The starting materials utilized in this preparative route are known or can be made in a known fashion.

Condensation of (a) protected compounds of Formula II with a protected compound of Formula III; (b) a protected compound of Formula IV with a protected compound of Formula V; or (c) a protected compound of Formula VI with a protected compound of Formula VII afford intermediates of Formula VIII:

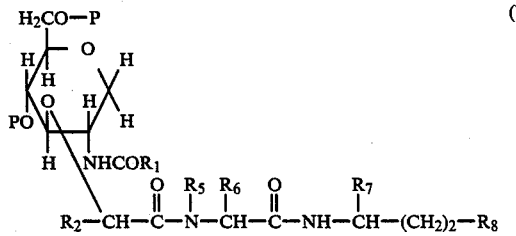
(VIII.)

wherein $R_1$, $R_2$, $R_5$, $R_6$, $R_7$, and $R_8$ have the meanings mentioned above.

Intermediates of Formula VIII are converted into compounds of Formula I, in those cases where $R_3$ and $R_4$ are hydrogen, by removal of the sugar hydroxyl and peptide carboxyl protecting groups, in a classical fashion, for example, by hydrogenolysis with hydrogen in the presence of a noble metal catalyst, such as palladium or platinum, or by acid hydrolysis.

In those cases where $R_3$ and/or $R_4$ are acyl, intermediates of Formula VIII are converted into compounds of Formula I by selective removal of the sugar hydroxyl protecting groups P, acylation of the C-4 and/or C-6 hydroxyls, and final removal of the remaining protecting group by hydrogenolysis with hydrogen in the presence of a noble metal catalyst, such as palladium or platinum.

In those cases where $R_3$ and/or $R_4$ are acyl, the compounds of Formula I are prepared by reaction of the deprotected intermediates of Formula VIII described above with the appropriate acid derivatives whereby condensation results in the desired 6-O- and/or 4-O-substituted compounds. All of the appropriate acid derivatives for preparing the compounds of Formula I are known compounds or may be prepared by known methods in an obvious manner. The condensation reaction will initially take place preferentially at the 6-position of the glucose ring. Then the reaction conditions are driven with the same or a different acid giving rise to 4-O, 6-O-diacylated derivatives wherein the acyl groups are the same or different. Where it is desired to prepare only the 4-O-acylated derivatives, the 6-position must be blocked while the 4-position acylation is carried out, followed by deblocking. The blocking and deblocking reactions may be carried out in accordance with procedures well known in the art.

The condensation reactions may be carried out in accordance with procedures well established in the art for preparing organic compounds. Thus, the condensation may be carried out using the carboxylic acid, the acid anhydride, or the acid halide.

Where the carboxylic acid is utilized, a coupling agent, for example N,N'-dicyclohexylcarbodiimide (DCC) in the presence of 4-dimethylaminopyridine (DMAP), will be employed. The reaction is carried out in an inert aprotic solvent, such as dimethylformamide, dimethylsulfoxide, or pyridine, at a temperature of from 0° to 50° C. for from 6 hours to 6 days.

Where the acid anhydride is utilized, a coupling agent may be employed, although this is not necessary. However, an acid acceptor, such as pyridine, 4-dimethylaminopyridine, or trimethylamine, should be used. The solvent medium in which the reaction is carried out and the other reaction conditions are the same as for the carboxylic acid condensation.

Where the acid halide is utilized, all of the reaction conditions are the same as those for the acid anhydride condensation.

Once the condensation reaction has been completed, the remaining protecting groups are readily removed by hydrogenolysis, preferably carried out with a catalyst such as palladium oxide in the presence of glacial acetic acid.

Compounds wherein $R_1$ is other than methyl are obtained from the known 2-acetamido-1,5-anhydro 2-deoxy-D-glucitol of Formula IX:

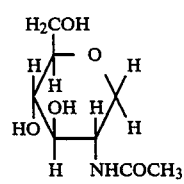
(IX.)

by (a) de-N-acetylation to give 2-amino-1,5-anhydro-2-deoxy-D-glucitol of Formula X:

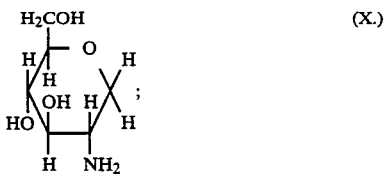

and by (b) N-acylation, (1) in the case where $R_1$ is alkyl or substituted-alkyl, with the appropriate alkanoic anhydride or alkanoyl halide, preferably chloride, or substituted-alkanoic anhydride or substituted-alkanoyl halide, preferably chloride, and (2) in the case where $R_1$ is phenyl or substituted phenyl, with the appropriate aroic anhydride or aroyl halide, preferably chloride, or substituted aroic anhydride or substituted aroyl halide, preferably chloride, under Schotten-Baumann conditions. The protecting groups are then introduced at the C-4, and C-6 positions to give a compound of Formula VI which may then be converted to a compound of Formula II or Formula IV.

Compounds wherein $R_6$ is other than methyl, may be obtained when, for example, one of the following amino acids is substituted for alanine:

| Amino acid | $R_6$ |
|---|---|
| serine | $CH_2OH$ |
| cysteine | $CH_2SH$ |
| phenylalanine | benzyl |
| tyrosine | p-hydroxybenzyl |
| valine | isopropyl |
| leucine | 2-methylpropyl |
| isoleucine | 1-methylpropyl |
a-aminobutyric | $CH_2CH_3$ |
| norvaline | $CH_2CH_2CH_3$ |
| norleucine | $CH_2CH_2CH_2CH_3$ |

Compounds wherein $R_5$ and $R_6$ together are —$CH_2CH_2CH_2$ are obtained by substituting proline for alanine.

EXAMPLE 1

Preparation of 2-acetamido-1,5-anhydro-2-deoxy-3-O-(D-2-propionyl-L-alanyl-D-isoglutamine)-D-glucitol Step A: Preparation of 2-acetamido 1,5 anhydro-4,6O-benzylidene-2-deoxy-D-glucitol A mixture of 2-acetamido-1,5-anhydro-2-deoxy-D-glucitol [prepared by the process set forth in D. Horton and M. L. Wolfrom, J. Org Chem., 27 (1962)1794] (500 mg., 2.4 mmol) and zinc chloride (700 mg.) in benzaldehyde (10 ml) was stirred with exclusion of moisture for 3 hrs. at room temperature. The product was precipitated by addition of water and hexane. The solid was filtered, washed with copious amounts of water and finally hexane, and dried in vacuo over phosphorus pentoxide to afford 2-acetamido-1,5 anhydro-4,6-O-benzylidene-2-deoxy-D-glucitol, yield 530 mg. (74%). The 300 MHz NMR spectrum in dimethylsulfoxide-d6 was in accord with the desired structure.

Step B: Preparation of 2-acetamido-1,5-anhydro-4,6-O-benzylidene-3-O-(D-1-carboxyethyl)-2-deoxy-D-glucitol To a solution of 2-acetamido-1,5-anhydro 4,6-O-benzylidene-2-deoxy-D-glucitol (530 mg., 1.8 mmol) in dry p dioxane (40 ml.) was added sodium hydride in oil suspension (177 mg.) (50% of sodium hydride by weight). After stirring for 1 hr. at 95°, the temperature was lowered to 65°, and a solution of L-2-chloropropionic acid (353 mg., 3.3 mmol) in a small volume of dioxane was added. The mixture was stirred for 1 hr. at 65° and then additional sodium hydride (710 mg.) and L-2-chloropropionic acid (353 mg.) were added. After stirring overnight at 65°, the mixture was cooled and then slowly added to cold 50% aqueous acetic acid (25 ml.) to decompose excess sodium hydride. The mixture was evaporated, the residue partitioned between dichloromethane and water, and the organic layer evaporated. The residue was dissolved in the minimal volume of chloroform, and the solution was applied to a column of silica gel (Merck No. 7734) that was eluted with 35:1:0.2 chloroform-methanol-acetic acid. The fractions containing the desired component were combined and evaporated to give 2-acetamido-1,5-anhydro-4,6-O-benzylidene-3-O-(D-1-carboxyethyl)-2-deoxy-D-glucitol as a solid that was dried in vacuo over phosphorus pentoxide; yield 210 mg. (32%). The 300 MHz NMR spectrum in dimethylsulfoxide d6 was in accord with the desired structure.

Step C: Preparation of 2-acetamido-1,5-anhydro-4,6-O-benzylidene-2-deoxy-3-O-(D-2-propionyl-L-alanyl-D-isoglutamine benzyl ester)-D-glucitol To a solution of 2-acetamido-1,5-anhydro-4,6-O-benzylidene-3-O-(D-1-carboxyethyl)-2-deoxy-D-glucitol (200 mg., 0.54 mmol) in dry N,N-dimethylformamide (2.3 ml) at −15° were added successively N-methylmorpholine (60 μl.) and isobutyl chloroformate (71 μl.). After stirring 3 minutes at 15°, a precooled solution of L-alanyl-D-isoglutamine benzyl ester hydrochloride (219 mg., 0.64 mmol) and N-methylmorpholine (70 μl.) in dry N,N-dimethylformamide (2.3 ml) was added. The mixture was stirred for 4 hours at −15° with exclusion of moisture. After the temperature was increased to 0°, 2.5M aqueous potassium hydrogen carbonate (1 ml.) was added, and the mixture was stirred for 30 minutes at 0°. The product was precipitated by addition of water ( 25 ml.). The solid was filtered, washed with water, dried by suction, and then in vacuo over phosphorus pentoxide to give pure 2-acetamido-1,5-anhydro-4,6-O-benzylidene-2-deoxy-3-O-D-2-propionyl-L-alanyl-D-isoglutamine benzyl ester)-D-glucitol; yield 320 mg. (89%). The 300 NMz NMR spectrum in dimethyl sulfoxide d6 was in accord with the desired structure.

Step D: Preparation of 2-acetamido-1,5-anhydro-2-deoxy-3-O-(D-2-propionyl-L-alanyl-D-isoglutamine)-D-glucitol A solution of 2-acetamido-1,5-anhydro 4,6-O-benzylidene-2-deoxy-3-O-(D-2-propionyl-L-alanyl-D-isoglutamine benzyl ester)-D-glucitol (100 mg., 0.15 mmol) in glacial acetic acid (8 ml.) was hydrogenolyzed for 4 hours at atmospheric pressure and room temperature in the presence of palladium (added as PdO, 200 mg.). The reaction mixture was filtered through Celite, the filtrate evaporated, and coevaporated several times with water, methanol, and toluene. The residue was dissolved in the minimal volume of methanol, and the product was precipitated by addition of diethyl ether. The solid was filtered, washed with ether, and dried in vacuo over phosphorus pentoxide to give 2-acetamido-1,5anhydro- 2-deoxy-3-O-(D-2-propionyl-L-alanyl-D-isoglutamine)D-glucitol; yield 69 mg. (95%). The 300 MHz NMR spectrum in deuterium oxide was in accord with the desired structure.

EXAMPLE 2

Preparation of 2-acetamido-1,5-anhydro-6-O-behenoyloxyisobutyryl 2-deoxy-3-O-(D-2-propionyl-L-alanyl-D-isoglutamine)-D-glucitol

Step A: Preparation of 2-acetamido-1,5-anhydro-2-deoxy-3-O-(D-2-propionyl-L-alanyl-D-isoglutamine benzyl ester)-D-glucitol A mixture of 2-acetamido-1,5-anhydro-4,6-O-benzylidene-2-deoxy-3-O-(D-2 propionyl-L-alanyl-D-isoglutamine benzyl ester)-D-glucitol (190 mg., 0.29 mmol) 30 in 60% aqueous acetic acid (8 ml.) was heated for 4 hours at 85°, cooled, evaporated, and coevaporated several times with toluene. Trituration of the residue with diethyl ether gave a solid that was filtered and dried in vacuo over phosphorus pentoxide; yield 162 mg. (99%). The 300 MHz NMR spectrum in dimethylsulfoxide-$d_6$ was in accord with the desired structure.

Step B: Preparation of 2-acetamido-1,5-anhydro-6-O-behenoyloxyisobutyryl-2-deoxy-3-O-(D-2 propionyl-L-alanyl-D-isoglutamine benzyl ester)-D-glucitol To a solution of behenoyloxyisobutyric acid (112 mg., 0.26 mmol) in dry N,N-dimethylformamide (3 ml) were added 4 dimethylaminopyridine (4 mg.) and 2-acetamido-1,5-anhydro-2-deoxy-3-O-(D-propionyl-L-alanyl-D-isoglutamine benzyl ester)-D-glucitol glucitol (150 Mg., 0.26 mmol). The mixture was cooled in an ice-bath, and N,N'-dicyclohexylcarbodiimide (DCC) (55 mg.) was added. The reaction mixture was stirred overnight at room temperature. Dichloromethane was added to the mixture to achieve solution. A second addition of behenoyloxyisobutyric acid (112 mg.) and DCC (55 mg.) was made and stirring was continued overnight. Again sufficient dichloromethane was added to cause solution. After a third addition of the acid and DCC and stirring for 72 hours at room temperature, the reaction mixture was concentrated, the residue was taken up in dichloromethane, washed twice with 0.5M hydrochloric acid, once with saturated aqueous sodium bicarbonate, once with water, and evaporated. The residue was dissolved in the minimal volume of chloroform, and the solution was applied to a column of silica gel (Merck No. 7734) that was eluted with 20:1 chloroform-methanol. Evaporation of the appropriate fractions gave 2-acetamido-1,5-anhydro6-O-behenoyloxyisobutyryl-2-deoxy-3-O-(D-2-propionyl-L-alanyl-D-isoglutamine benzyl ester)-D-glucitol as a solid; yield 144 mg. (56%). The 300 MHz NMR spectrum in dimethylsulfoxide $d_6$ was in accord with the desired structure.

Step C: Preparation of 2-acetamido 1,5 anhydro-6-O-behenoyloxyisobutyryl 2-deoxy 3-O-(D-2-propionyl-L-alanyl-D-isoglutamine)-D-glucitol A solution of 2-acetamido-1,5-anhydro 6-O- behenoyloxyisobutyryl-2-deoxy-3-O-(D-2-propionyl-L-alanyl-D-isoglutamine benzyl ester)-D-glucitol (140 mg., 0.14 mmol) in glacial acetic acid (5 ml.) was hydrogenolyzed overnight at atmospheric pressure and room temperature in the presence of palladium (added as PdO, 150 mg.). The catalyst was removed by filtration through Celite, the filtrate evaporated and coevaporated several times with toluene. The residue was dissolved in the minimal volume of chloroform, and the solution was applied to a column of silica gel (Merck No. 7734) that was eluted with initially 9:1 chloroform-methanol and subsequently 40:10:1 chloroform-methanol-water. Evaporation of the appropriate fractions and coevaporation several times with diethyl ether gave 2-acetamido-1,5-anhydro-6-O-behenoyloxyisobutyryl-2-deoxy-3-O-(D-2 propionyl-L-alanyl-D-isoglutamine)-D-glucitol as a solid that was dried in vacuo over phosphorus pentoxide; yield 105 mg. (83%). The 300 MHz NMR spectrum in dimethylsulfoxide $d_6$ was in accord with the desired structure.

It is reasonably believed on the basis of the data that the disclosed pharmaceutical compounds herein will provide a human host who is immunocompromised as a result of infection or contact with an AIDS-related virus, with enhanced host resistance to "opportunistic" bacterial, fungal and viral infections, including the conditions of Kaposi's sarcoma and Pneumocystis pneumonia.

What is claimed is:

1. A composition for enhancing host resistance against opportunistic bacterial, fungal and viral infection in an AIDS-immunocompromised human host comprising a compound of the formula:

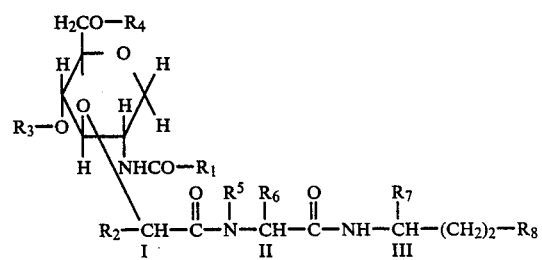

wherein:
$R_1$ is $C_{1-7}$ alkyl, substituted $C_{1-7}$ alkyl; phenyl; or substituted phenyl;
$R_2$ is hydrogen; or $C_{1-10}$ alkyl;
$R_3$ and $R_4$ may be the same or different and are each independently hydrogen, or acyl of the formula:

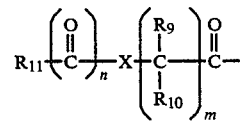

where X is —O—, —S—, —CH$_2$—, or —N—;
   |
   $R_{12}$ $R_9$, $R_{10}$, and $R_{12}$ may be the same or different and are each independently hydrogen; $C_{1-20}$ alkyl; $C_{2-20}$ alkenyl; $C_{1-20}$ alkylcarbonyloxy; amino; phenyl; benzyl; $C_{1-20}$alkoxymethyl; or $C_{1-20}$ alkylamido;
$R_{11}$ is hydrogen; $C_{1-30}$alkyl; $C_{2-30}$ alkenyl; $C_{1-30}$ alkoxy; phenyl; $C_{1-20}$ alkylsulfonyl; or cholesteryl;
and m is 0–90; and n is 0 or 1, provided that when n is 0, $R_1$ may additionally be phenyl, substituted phenyl, 1-adamantyl, or heterocycle selected from the group consisting of 2- or 3-furyl, 2- or 3- thienyl, 2- or 3-pyrrolidinyl, 2-, 3-, or 4-pyridyl, and 1-tetrazolyl, said heterocycle optionally substituted with $C_{1-20}$ alkylcarbonyl;

$R_5$ is hydrogen; or $R_5$-$R_6$ together is —$CH_2$—$CH_2$—$CH_2$;

$R_6$ is hydrogen; $C_{1-7}$ alkyl, hydroxymethyl; mercaptomethyl; benzyl; or substituted benzyl;

$R_7$ and $R_8$ may be the same or different and are each independently COOR or CONR'R", where R is hydrogen or $C_{l-7}$ alkyl, and R' and R" are each independently hydrogen or $C_{1-3}$ alkyl;

when $R_2$ is $C_{1-10}$ alkyl, the stereochemistry at asymmetric center I can be either D or L; when $R_6$ is not hydrogen, the stereochemistry at asymmetric center II is L; the stereochemistry at asymmetric center III is D; or pharmaceutically acceptable acid addition salts thereof; and an anti-viral, anti-AIDS drug selected from the group consisting of azidothymidine, ansamycin, ribavarin, deoxycytdine, HPA-23, AL-721, and foscarnet; in a physiologically acceptable medium in an amount effective to impart resistance against opportunistic infection.

2. The compound according to claim 1 wherein the compound is 2-acetamido-1,5-anhydro-2-deoxy-3-O-(D-2-propionyl-L-alanyl-D-isoglutamine)-D-glucitol.

3. The compound according to claim 1 wherein the compound is 2-acetamido-1,5-anhydro-6-O-behenoyloxyisobutyryl-2-deoxy-3-O-(D-2-propionyl-L-alanyl-D-isoglutamine)-D-glucitol.

4. A method for enhancing host resistance against opportunistic bacterial, fungal and viral infection in an AIDS-immunocompromised human host comprising the step of administering to said host a composition comprising a compound according to claim 1.

* * * * *